US012649010B2

(12) United States Patent
 Childress

(10) Patent No.: US 12,649,010 B2
(45) Date of Patent: Jun. 9, 2026

(54) SYSTEMS AND METHODS FOR SANITIZATION OF INDIVIDUALS WITH ULTRAVIOLET LIGHT

(71) Applicant: The Boeing Company, Chicago, IL (US)

(72) Inventor: Jamie J. Childress, Seattle, WA (US)

(73) Assignee: THE BOEING COMPANY, Arlington, VA (US)

( * ) Notice: Subject to any disclaimer, the term of this patent is extended or adjusted under 35 U.S.C. 154(b) by 680 days.

(21) Appl. No.: 17/709,091

(22) Filed: Mar. 30, 2022

(65) Prior Publication Data

US 2022/0354980 A1    Nov. 10, 2022

Related U.S. Application Data

(60) Provisional application No. 63/183,647, filed on May 4, 2021.

(51) Int. Cl.
 *A61L 2/24* (2006.01)
 *A61L 2/10* (2026.01)
  (Continued)

(52) U.S. Cl.
 CPC *A61L 2/24* (2013.01); *A61L 2/10* (2013.01); *A61L 9/20* (2013.01); *A61L 2103/75* (2026.01);
  (Continued)

(58) Field of Classification Search
 CPC . A61B 5/1113; A61L 2/10; A61L 2/24; A61L 9/20
 See application file for complete search history.

(56) References Cited

U.S. PATENT DOCUMENTS 5,483,127 A    1/1996  Widmayer
6,877,248 B1   4/2005  Cross et al.
  (Continued)

FOREIGN PATENT DOCUMENTS

CA    2777014    4/2011
CA    2904971    7/2016
  (Continued)

OTHER PUBLICATIONS

"Jetson Nano Developer Kit", accessible at https://developer.nvidia.com/embedded/jetson-nano-developer-kit (dated at least prior to May 4, 2021).
  (Continued)

*Primary Examiner* — Sean E Conley
*Assistant Examiner* — Eric Talbert
(74) *Attorney, Agent, or Firm* — MH2 Technology Law Group LLP

(57) ABSTRACT

A sanitization system for a space includes an ultraviolet (UV) light source configured to emit UV light towards a UV light zone at a UV light level, a motion sensor device configured to sense movements of one or more individuals, and a controller. The controller is configured to determine, based on the movements of the one or more individuals, an exposure parameter value for each of the one or more individuals in the UV light zone, determine that the value of the exposure parameter determined for at least one of the one or more individuals exceeds a threshold value, and, responsive to determining that the value of the exposure parameter determined for the at least one of the one or more individuals exceeds the threshold value, cause the UV light source to reduce the UV light level of the UV light emitted towards the UV light zone.

20 Claims, 6 Drawing Sheets

(51) Int. Cl.
  *A61L 9/20* (2006.01)
  *A61L 103/75* (2026.01)

(52) U.S. Cl.
  CPC ........ *A61L 2202/11* (2013.01); *A61L 2202/14* (2013.01); *A61L 2209/111* (2013.01)

(56) References Cited

U.S. PATENT DOCUMENTS

| | | | |
|---|---|---|---|
| 8,084,752 | B2 | 12/2011 | Ranta et al. |
| 8,138,690 | B2 | 3/2012 | Chemel et al. |
| 8,339,069 | B2 | 12/2012 | Chemel et al. |
| 8,368,321 | B2 | 2/2013 | Chemel et al. |
| 8,543,249 | B2 | 9/2013 | Chemel et al. |
| 8,552,664 | B2 | 10/2013 | Chemel et al. |
| 8,593,135 | B2 | 11/2013 | Chemel et al. |
| 8,805,550 | B2 | 8/2014 | Chemel et al. |
| 8,954,170 | B2 | 2/2015 | Chemel et al. |
| 9,623,133 | B2 | 4/2017 | Childress et al. |
| 9,700,072 | B2 | 7/2017 | Dobrinsky et al. |
| 9,783,974 | B1 | 10/2017 | Tillotson |
| 9,855,353 | B1 | 1/2018 | Stacy |
| 9,993,571 | B2 | 6/2018 | Lin et al. |
| 10,130,727 | B1 | 11/2018 | Byrnes et al. |
| 10,145,055 | B1 | 12/2018 | Harlan et al. |
| 10,272,169 | B2 | 4/2019 | Lin et al. |
| 10,301,806 | B2 | 5/2019 | Childress et al. |
| 2006/0163135 | A1 | 7/2006 | Ellis et al. |
| 2010/0193629 | A1 | 8/2010 | Breit et al. |
| 2011/0057123 | A1 | 3/2011 | Ho |
| 2011/0155915 | A1 | 6/2011 | Brueck et al. |
| 2012/0282135 | A1 | 11/2012 | Trapani |
| 2013/0330235 | A1 | 12/2013 | Stibich et al. |
| 2014/0059796 | A1 | 3/2014 | Boodaghians et al. |
| 2014/0266695 | A1 | 9/2014 | Addison et al. |
| 2016/0030766 | A1* | 2/2016 | Scritchfield .......... G06V 40/107 607/91 |
| 2016/0088868 | A1 | 3/2016 | Dobrinsky et al. |
| 2016/0195427 | A1 | 7/2016 | Vance et al. |
| 2016/0220716 | A1 | 8/2016 | Childress et al. |
| 2016/0250362 | A1 | 9/2016 | Mackin |
| 2017/0107659 | A1 | 4/2017 | Hills |
| 2017/0246329 | A1* | 8/2017 | Lloyd ........................ A61L 2/10 |
| 2017/0283062 | A1 | 10/2017 | Childress |
| 2017/0283092 | A1 | 10/2017 | Brown et al. |
| 2017/0284076 | A1 | 10/2017 | Jensen |
| 2018/0050122 | A1 | 2/2018 | Lin et al. |
| 2018/0051447 | A1 | 2/2018 | Hills et al. |
| 2018/0064833 | A1 | 3/2018 | Childress et al. |
| 2018/0079528 | A1 | 3/2018 | Siegmeth et al. |
| 2018/0084956 | A1 | 3/2018 | Childress |
| 2018/0369434 | A1 | 12/2018 | Callahan |
| 2018/0369439 | A1 | 12/2018 | Brockschmidt et al. |
| 2018/0371733 | A1 | 12/2018 | Childress et al. |
| 2018/0373157 | A1 | 12/2018 | Kimsey-Lin |
| 2019/0171111 | A1 | 6/2019 | Kimsey-Lin |
| 2020/0282087 | A1* | 9/2020 | Latif ......................... A61L 2/10 |
| 2021/0052757 | A1* | 2/2021 | Baarman .................. A61L 2/10 |

FOREIGN PATENT DOCUMENTS

| | | | |
|---|---|---|---|
| DE | 19824423 | | 12/1999 |
| JP | H08 31585 | | 2/1996 |
| JP | 2002263645 | | 9/2002 |
| KR | 102229676 | B1 * | 3/2021 ............... A61L 2/18 |
| WO | 99/62567 | | 12/1999 |
| WO | 2018041986 | A1 | 3/2018 |

OTHER PUBLICATIONS

European Search Report prepared by the European Patent Office in application No. EP 22 16 4825 dated Sep. 9, 2022.

Notice of Reasons for Rejection for related Application JP2022-072363, as issued by the Japanese Patent Office Jan. 13, 2026.

Chinese Office Action for CN Application No. 202210434917.7, dated Mar. 20, 2026.

* cited by examiner

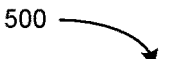

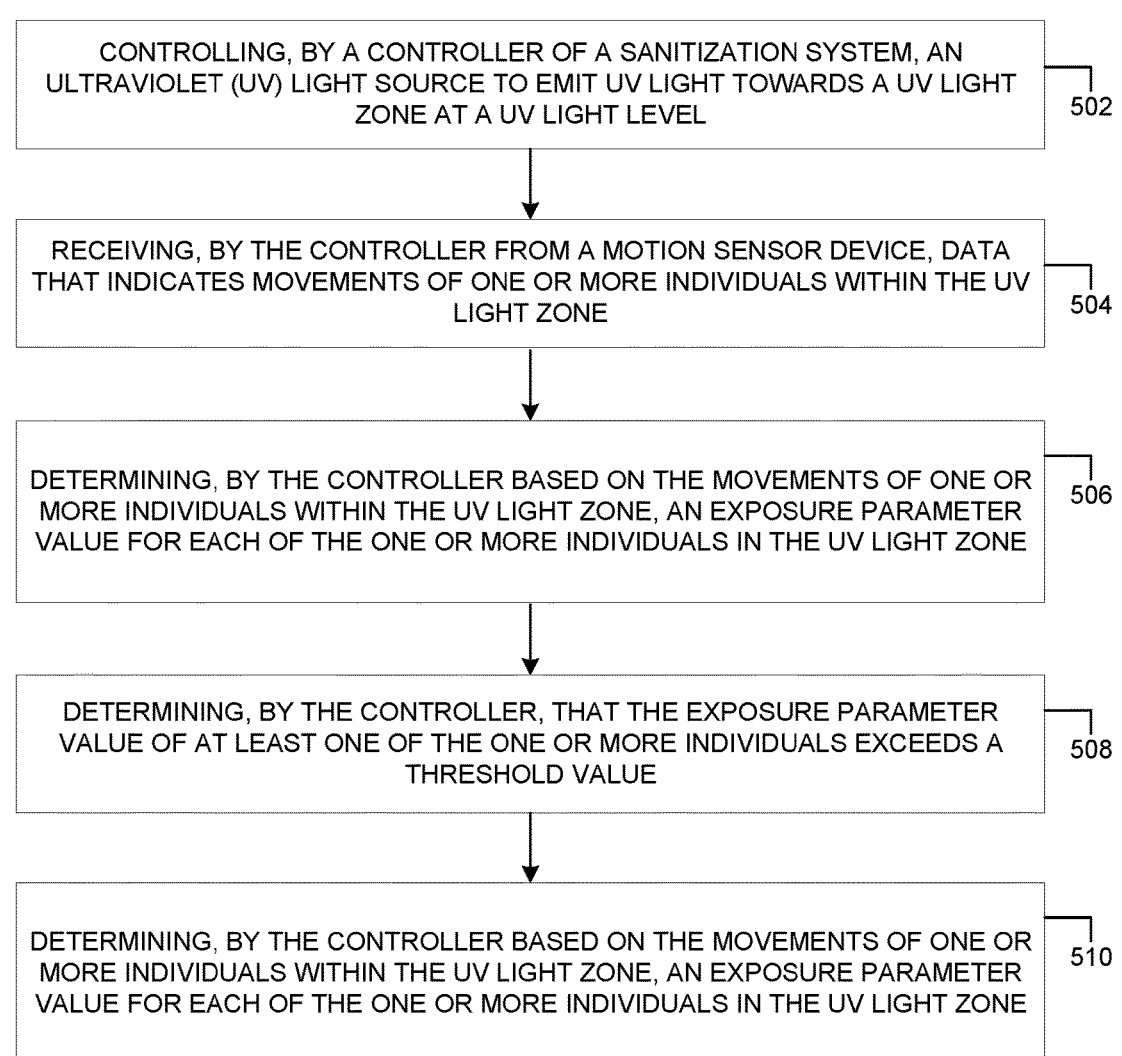

CONTROLLING, BY A CONTROLLER OF A SANITIZATION SYSTEM, AN ULTRAVIOLET (UV) LIGHT SOURCE TO EMIT UV LIGHT TOWARDS A UV LIGHT ZONE AT A UV LIGHT LEVEL
502

RECEIVING, BY THE CONTROLLER FROM A MOTION SENSOR DEVICE, DATA THAT INDICATES MOVEMENTS OF ONE OR MORE INDIVIDUALS WITHIN THE UV LIGHT ZONE
504

DETERMINING, BY THE CONTROLLER BASED ON THE MOVEMENTS OF ONE OR MORE INDIVIDUALS WITHIN THE UV LIGHT ZONE, AN EXPOSURE PARAMETER VALUE FOR EACH OF THE ONE OR MORE INDIVIDUALS IN THE UV LIGHT ZONE
506

DETERMINING, BY THE CONTROLLER, THAT THE EXPOSURE PARAMETER VALUE OF AT LEAST ONE OF THE ONE OR MORE INDIVIDUALS EXCEEDS A THRESHOLD VALUE
508

DETERMINING, BY THE CONTROLLER BASED ON THE MOVEMENTS OF ONE OR MORE INDIVIDUALS WITHIN THE UV LIGHT ZONE, AN EXPOSURE PARAMETER VALUE FOR EACH OF THE ONE OR MORE INDIVIDUALS IN THE UV LIGHT ZONE
510

FIGURE 5

SYSTEMS AND METHODS FOR SANITIZATION OF INDIVIDUALS WITH ULTRAVIOLET LIGHT

CROSS-REFERENCE TO RELATED APPLICATIONS

The present application claims the benefit of U.S. Provisional Application No. 63/183,647, filed May 4, 2021, the contents of which is hereby incorporated by reference in its entirety.

FIELD

The present disclosure generally relates to systems and methods for light systems, and more particularly to systems and methods for operating ultraviolet (UV) light sources to disinfect an environment.

BACKGROUND

Pathogens may be spread between humans, between animals, or between humans and animals in many different ways. Consequently, there is an increasing need for the disinfection of public environments. One approach for disinfecting an environment involves irradiating the environment with ultraviolet (UV) light using UV light sources.

SUMMARY

In an example, a sanitization system for a space is described. The sanitization system includes, an ultraviolet (UV) light source configured to emit UV light towards a UV light zone at a UV light level, a motion sensor device configured to sense movements of one or more individuals in the UV light zone, and a controller in communication with the motion sensor device and the UV light source. The controller is configured to, determine, based on the movements of the one or more individuals sensed by the motion sensor device, an exposure parameter value for each of the one or more individuals in the UV light zone, determine that the value of the exposure parameter determined for at least one of the one or more individuals exceeds a threshold value, and, responsive to determining that the value of the exposure parameter determined for the at least one of the one or more individuals exceeds the threshold value, cause the UV light source to reduce the UV light level of the UV light emitted towards the UV light zone.

In another example, a method for sanitizing a space is described. The method includes controlling, by a controller of a sanitization system, an ultraviolet (UV) light source to emit UV light towards a UV light zone at a UV light level. The method includes receiving, by the controller from a motion sensor device, data that indicates movements of one or more individuals within the UV light zone. The method includes determining, by the controller based on the movements of one or more individuals within the UV light zone, an exposure parameter value for each of the one or more individuals in the UV light zone. The method includes determining, by the controller, that the exposure parameter value of at least one of the one or more individuals exceeds a threshold value. The method includes responsive to determining that the exposure parameter value of at least one of the one or more individuals exceeds the threshold value, causing, by the controller, the UV light source to reduce the UV light level of the UV light emitted towards the UV light zone.

In another example, a non-transitory computer readable medium is described. The non-transitory computer readable medium has instructions stored thereon that, when executed by one or more processors, cause a controller of a sanitization system to perform functions. The functions include controlling an ultraviolet (UV) light source to emit UV light towards a UV light zone at a UV light level. The functions include receiving, from a motion sensor device, data that indicates movements of one or more individuals within the UV light zone. The functions include determining, based on the movements of one or more individuals within the UV light zone, an exposure parameter value for each of the one or more individuals in the UV light zone. The functions include determining that the exposure parameter value of at least one of the one or more individuals exceeds a threshold value. The functions include, responsive to determining that the exposure parameter value of at least one of the one or more individuals exceeds the threshold value, causing the UV light source to reduce the UV light level of the UV light emitted towards the UV light zone.

The features, functions, and advantages that have been discussed can be achieved independently in various examples or may be combined in yet other examples. Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

FIG. 5 illustrates a flowchart of a method for sanitizing a space, according to an example implementation.

DETAILED DESCRIPTION

Figure 1:
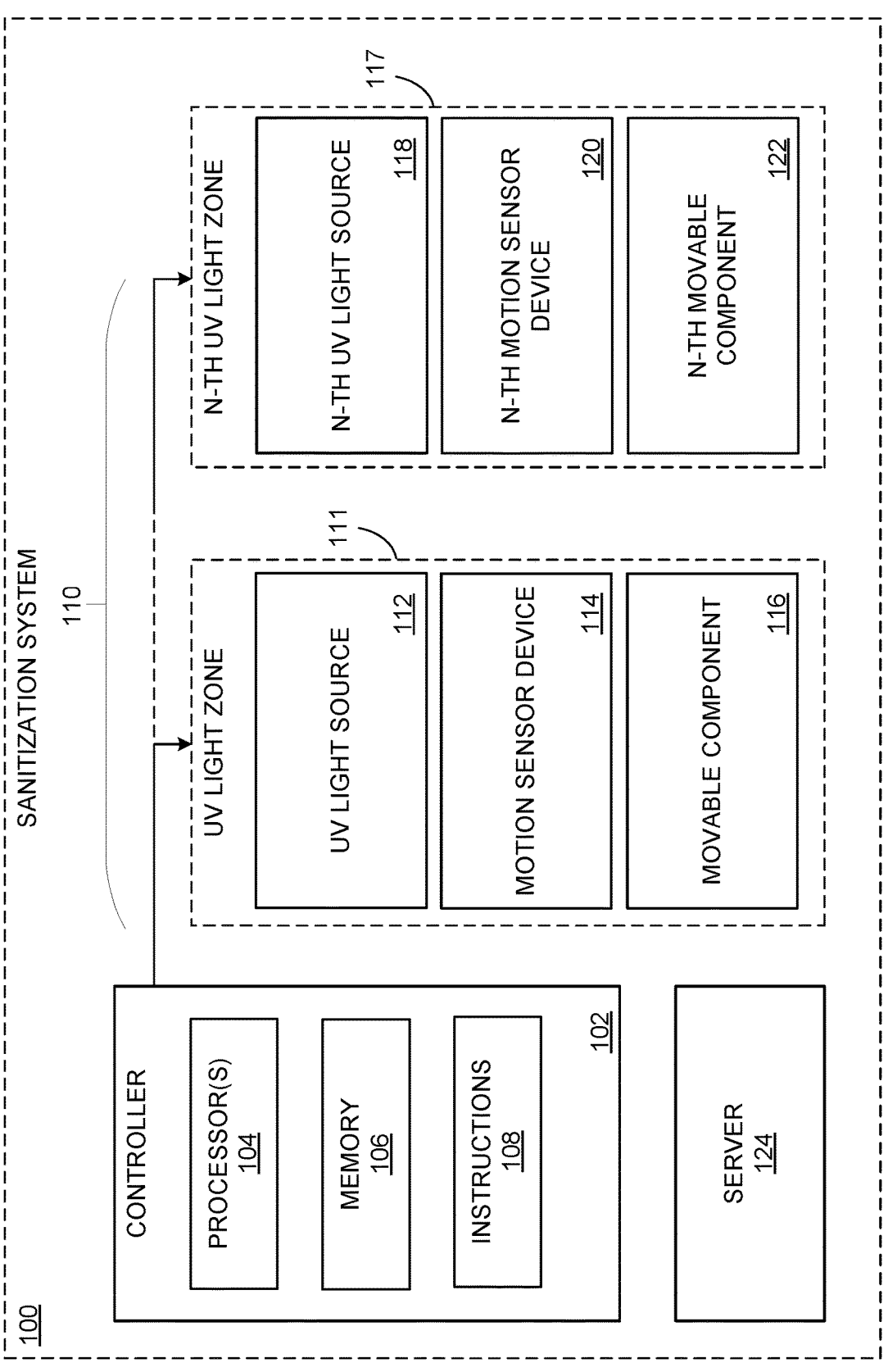
FIG. 1 illustrates a block diagram of a sanitization system, according to an example implementation.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Example systems and methods for sanitizing a space are described. In these examples, a plurality of individuals may enter the space. For example, a public space (e.g., a building, a part of a building, an outdoor area, or another environment) may include many people who enter and exit the space at different times, remain in the space for different amounts of time, and move within the space differently. When sanitizing a space using UV light, these differences between individuals result in different levels of exposure to UV light.

Emitting UV light at an area with a plurality of individuals disinfects surfaces and air between the individuals. Accordingly, emitting UV light towards a space, particularly congested areas of the space, may effectively eliminate or mitigate pathogens in an environment. However, it is also desirable to limit a level of UV light exposure experienced by each individual. In order to ensure that the space is effectively disinfected while also limiting UV light exposure for individuals in the space, the sanitization system tracks each individual user.

Within examples, a sanitization system is configured to track one or more UV exposure parameters (e.g., total exposure levels) for each individual in a UV light zone (e.g., an area in which UV light is emitted). This allows the sanitization system to adjust when, where, and how much UV light is emitted within the space in order to control the amount of UV light emitted toward each individual. As used herein, the term "exposure level" refers to an amount of incident light directed towards a given area over a period of time. For example, the exposure level may be represented in terms of joules/meter$^2$. An exposure level for an individual may be determined using a light level of a UV light source, an amount of time that the individual is exposed to UV light, and an area associated with an individual (e.g., a 0.5 m$^2$).

Within examples, the sanitization system includes a UV light source configured to emit UV light towards a UV light zone. The sanitization system also includes a motion sensor device configured to sense movements of one or more individuals in the UV light zone. The sanitization system also includes a controller in communication with the motion sensor device and the UV light source. The controller uses data from the sensor device to determine movements of the individuals, allowing the controller to determine a level of UV light exposure for each individual and to adjust aspects of emitting light using the UV light. For example, a UV light level may be reduced in a UV light zone if an exposure parameter value for at least one individual exceeds a threshold value. In alternative or additional examples, a direction of the UV light emitted by the UV light source may be adjusted to avoid the at least one individual with an exposure parameter value that exceeds the threshold value. The controller can cause the UV light source to emit light in other ways as well. By dynamically adjusting how the UV light source emits light, the sanitization system resolves issues that are particular to sanitization using UV light.

Referring now to the figures, FIG. 1 illustrates a block diagram of a sanitization system, according to an example implementation. In particular, FIG. 1 shows a sanitization system 100 for a space. In the depicted example, the sanitization system 100 includes a controller 102 and a plurality of UV light zones 110. Each UV light zone corresponds to a section of the space in which to emit UV light. For example, each UV light zone may be placed in portions of the space that are expected to be relatively congested, such as queue lines, hallways, doorways, or the like. The plurality of UV light zones 110 includes a UV light zone 111 and an n-th UV light zone 117. The sanitization system 100 may include more or fewer UV light zones.

The sanitization system 100 can be a computing system that includes one or more computing devices, such as the controller 102. For example, the controller 102 can be a central controller of the sanitization system 100, and can interact with one or more additional computing devices to perform functions. The controller 102 includes processor(s) 104, a memory 106, instructions 108.

The processor(s) 104 may be general-purpose processors or special purpose processors (e.g., digital signal processors, application specific integrated circuits, etc.). Processor(s) 104 are configured to execute the instructions 108 stored in the memory 106 to provide the functionality of the controller 102 and related systems and methods described herein.

The memory 106 may include or take the form of one or more computer-readable storage media that can be read or accessed by processor(s) 104. The computer-readable storage media can include volatile and/or non-volatile storage components, such as optical, magnetic, organic or other memory or disc storage, which can be integrated in whole or in part with processor(s) 104. In some examples, memory 106 can be implemented using a single physical device (e.g., one optical, magnetic, organic or other memory or disc storage unit), while in other examples, memory 106 can be implemented using two or more physical devices. The memory 106 thus is a non-transitory computer readable storage medium, and the instructions 108 are stored thereon. The instructions 108 include computer executable code. For example, the instructions 108 may specify how each function of the controller 102 is to be performed.

Each UV light zone includes a UV light source, a motion sensor device, and a movable component. Each UV light source may be a light emitting device that emits light in the UV spectrum (e.g., about 100-400 nm). For example, each UV light source may include one or more of a UV lamp, a UV light emitting diode (LED), or a UV laser. Each motion sensor device includes a sensor configured to track positions of one or more objects. For example, each motion sensor device may include a proximity sensor, an infrared (IR) tracking sensor, an image capture device (e.g., a camera), a light detection and ranging (LIDAR) device, or another device capable of tracking positions of individuals in the UV light zone. The movable component includes one or more of a switch, a servo, an actuator, an aperture, or another device configured to cause the UV light source to adjust a direction, beam angle, or beam spread of UV light emitted by the UV light source. The UV light zone 111 includes a UV light source 112, a motion sensor device 114, and a movable component 116. The n-th UV light zone 117 includes an n-th UV light source 118, an n-th motion sensor device 120, and an n-th movable component 122. Though each of these components are depicted as being within a UV light zone, the components may be physically located outside the UV light zone.

The first UV light zone and 111 the n-th UV light zone 117 may be separate UV light zones within the space. In order to manage UV light exposure levels for each individual within the space, the controller 102 may track one or more exposure parameters (e.g., total time exposed to UV light or total UV light exposure level) for individual users across each respective UV light zone. To facilitate this, a server 124 may be used for storing exposure parameter values for each user and characteristics of UV light emission in each UV light zone. The controller 102 may access this information to determine control instructions for respective UV light sources in the sanitization system 100. In this manner, for example, the controller 102 can control the n-th UV light source 118 based on UV light exposure of an individual in the UV light zone 111.

Other configurations of the sanitization system 100 are possible. For example, more or fewer UV light zones may be included in the space. Further, a controller may by dedicated to each UV light zone. Within example, the controller 102 may be a computing device within the server 124, or may be directly connected to one or both of a motion sensor device and a UV light source.

Accordingly, FIG. 1 shows that the sanitization system 100 includes a UV light source (e.g., the UV light source 112) configured to emit UV light towards a UV light zone at a UV light level, a motion sensor device (e.g., the motion sensor device 114) configured to sense movements of one or more individuals in the UV light zone, and a controller (e.g., the controller 102) in communication with the motion sensor device and the UV light source. The controller is configured to determine, based on the movements of the one or more individuals sensed by the motion sensor device, an exposure parameter value for each of the one or more individuals in the UV light zone. The controller is further configured to determine that the value of the exposure parameter determined for at least one of the one or more individuals exceeds a threshold value. The controller is further configured to, responsive to determining that the value of the exposure parameter determined for the at least one of the one or more individuals exceeds the threshold value, cause the UV light source to reduce the UV light level of the UV light emitted towards the UV light zone. Other functionality of sanitization systems are described below with respect to FIGS. 2-5. The sanitization system 100, the controller 102, or portions thereof are configured to carry out this functionality, either individually or in conjunction with other devices or systems. Further details of sanitizing a space using UV light are provided below with respect to FIGS. 2-5.

Figure 2:
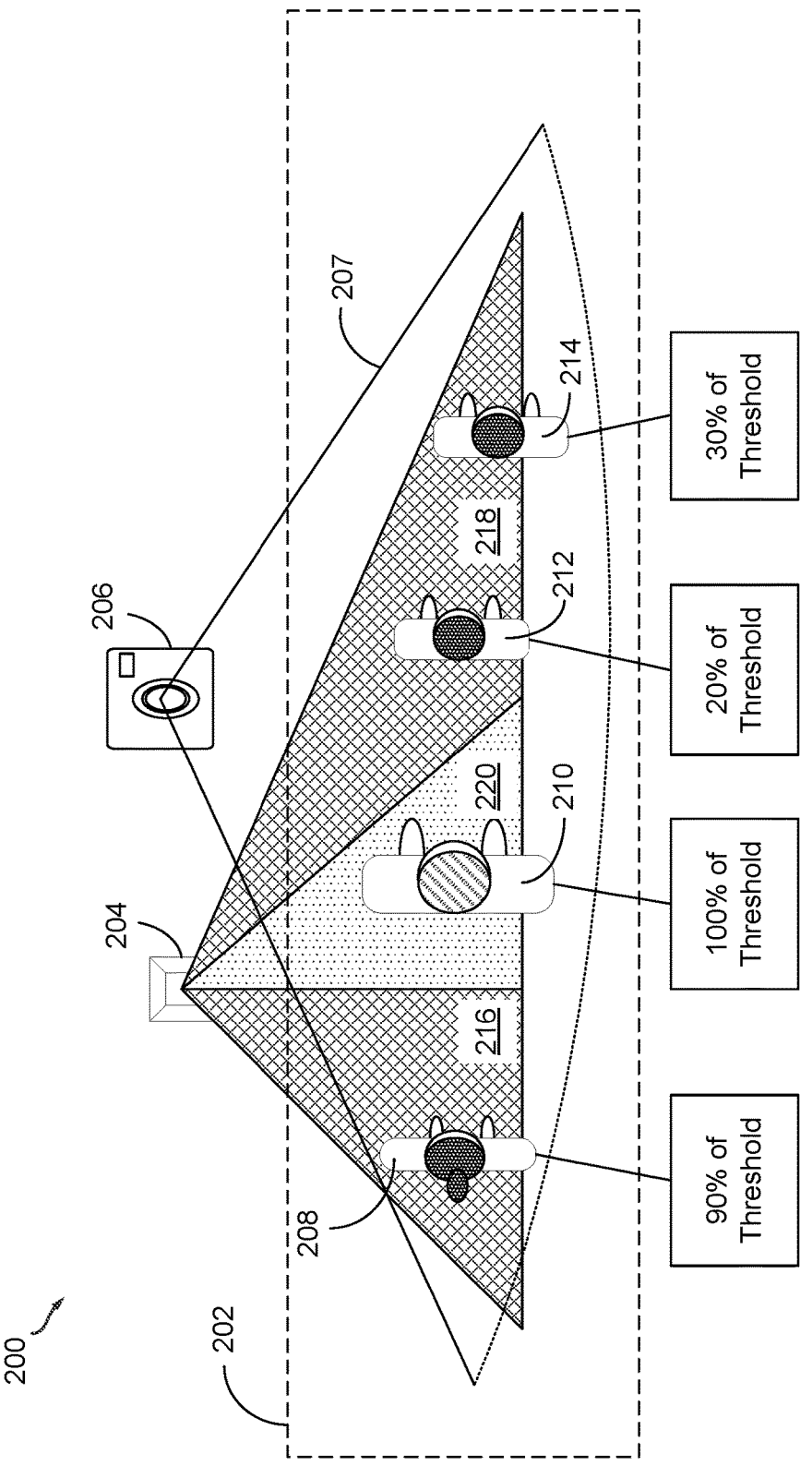
FIG. 2 illustrates a sanitization system operating in an environment, according to an example implementation.

FIG. 2 illustrates a sanitization system operating in an environment, according to an example implementation. In particular, FIG. 2 shows a top view of a space 200 that includes a UV light zone 202. The sanitization system includes a UV light source (e.g., the UV light source 112 in FIG. 1) configured to emit UV light towards the UV light zone 202 at a UV light level (e.g., a brightness level or power level of emitted UV light), a motion sensor device 206 configured to sense movements of one or more individuals in the UV light zone 202, and a controller (not shown). The UV light zone 202 includes a plurality of individuals in a queue. The plurality of individuals includes a first individual 208, a second individual 210, a third individual 212, and a fourth individual 214.

The sanitization system is configured to detect movements of each individual in the UV light zone. For example, the motion sensor device 206 is depicted as an image capture device that has a field of view 207 that covers the UV light zone 202. Within examples, the sanitization system can use facial recognition techniques to track the positions of individuals in the UV light zone 202 based on images captured by the motion sensor device 206. By determining a first position of a respective individual in the UV light zone 202 at a first time, and determining a second position of the respective individual in the UV light zone 202 at a second time, the motion sensor device and the sanitization system can detect movement of the respective individual within the UV light zone 202. Other ways of detecting movements of individual users are possible. For example, a proximity sensor, LIDAR device, and/or another device configured to sense movement can be used to allow the sanitization system to detect movements of the individuals.

The sanitization system determines an exposure parameter value for each individual. For example, the exposure parameter value may be an amount of time that an individual is exposed to UV light, a total exposure level, or another parameter for quantifying how much UV light is emitted toward the individual. The exposure parameter value may be compared to a threshold value to determine how to control the UV light source 204. For example, the threshold value can be set based on a Threshold Limit Value for UV exposure (e.g., a value lower than the Threshold Limit Value). The threshold value may be determined based on one or more characteristics of the UV light source 204. For example, the Threshold Limit Value may vary depending on the wavelength or range of wavelengths of UV light emitted by the UV light source 204, and the threshold value may be set based on the wavelength or range of wavelengths of UV light emitted by the UV light source 204.

In FIG. 2, the first individual 208 has reached 90% of the threshold value, the second individual 210 has reached 100% of the threshold value, the third individual 212 has reached 20% of the threshold value, and the fourth individual 214 has reached 30% of the threshold value. Different individuals may have different exposure levels based on how long they have been in one or more UV light zones in the space 200. Because the exposure parameter value of the second individual 210 has reached the threshold value, the controller of the sanitization system causes the UV light source to reduce a UV light level in the UV light zone 202.

Within examples, reducing the UV light level may include causing the UV light source 204 to stop emitting light toward the UV light zone 202 altogether. In other examples, reducing the UV light level may include causing the UV light source 204 to reduce an intensity or brightness of the emitted UV light. For example, the threshold value may be a first threshold of a plurality of thresholds, and each threshold value may correspond to a different light level. In this manner, the sanitization system can ensure that some level of UV light is emitted by the UV light source 204 until an individual approaches a final threshold value (e.g., a threshold slightly below a Threshold Limit Value of UV light exposure). In still other examples, reducing the UV light level may include causing the UV light source 204 to avoid emitting UV light toward a respective individual that has reached the threshold value while continuing to emit UV light toward other portions of the UV light zone 202. In FIG. 2, the UV light source 204 continues to emit UV light towards a first section 216 and a second section 218 of the UV light zone 202 at a first UV light level, and the UV light source 204 reduces the UV light level of UV light emitted towards a third section 220 to a second UV light level. In this manner, the sanitization system can ensure that individuals that have an exposure parameter value below the threshold value (e.g., the first individual 208, the third individual 212, and the fourth individual 214) continue to be exposed to UV light while an individual that has an exposure parameter value at or above the threshold value (e.g., the second individual 210) is exposed to a lower level of UV light.

Figure 3A:
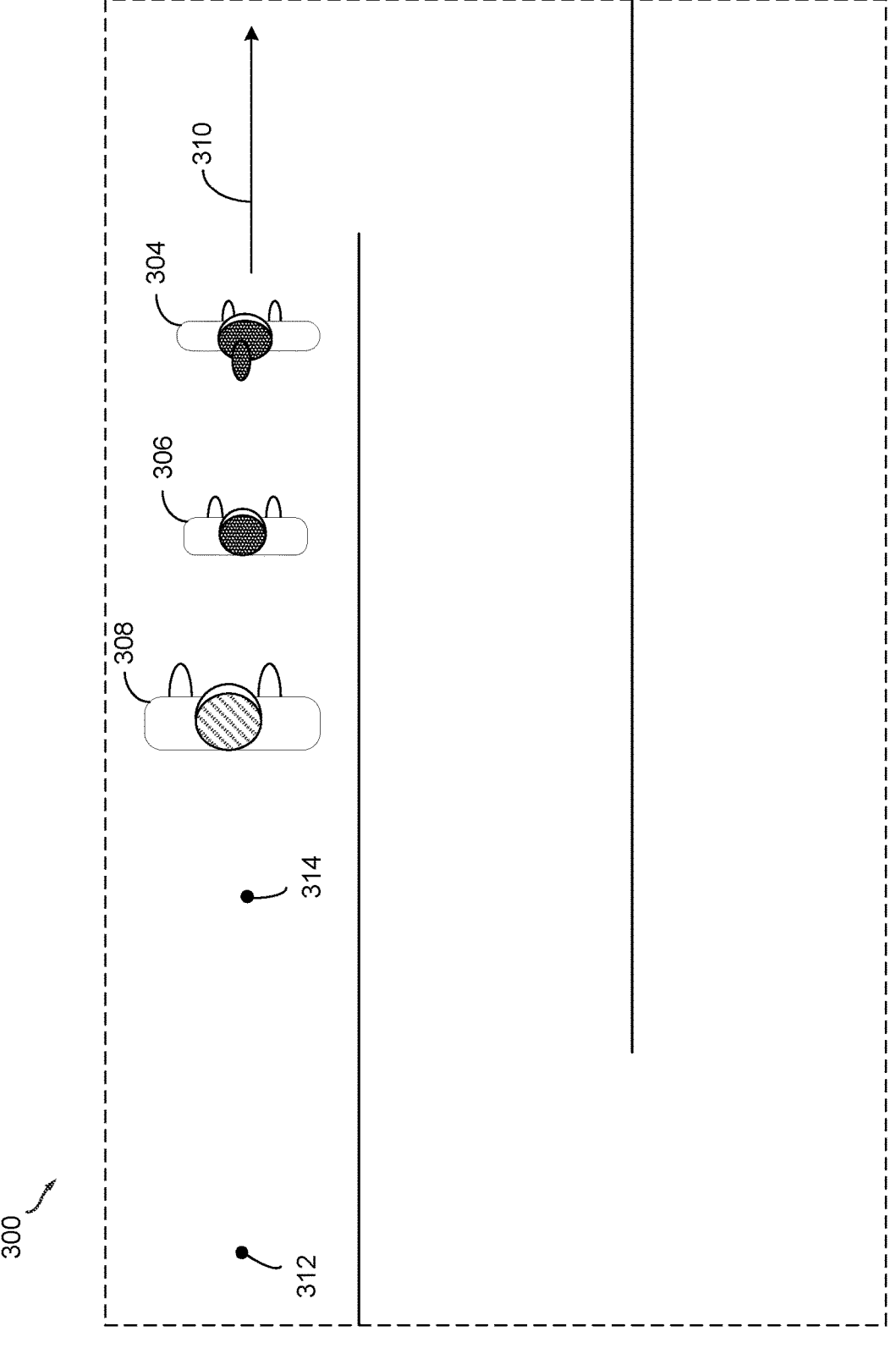
FIG. 3A illustrates a UV light zone at a first time, according to an example implementation.

FIG. 3A illustrates a UV light zone at a first time, according to an example implementation. In particular, FIG. 3A shows a UV light zone 300 that covers at least part of a queue of individuals. The queue of individuals includes a first individual 304, a second individual 306, and a third individual 308. A sanitization system (not shown) may determine control instructions of a UV light source (not shown) based on how quickly the queue is moving. For example, the sanitization system or a controller thereof may determine a group flow velocity of the individuals in the queue based on movements of the one or more individuals sensed by a motion sensor device. Determining the group flow velocity may include determining an average period of time for the one or more individuals to move from a first point 312 of the UV light zone 300 to a second point 314 of the UV light zone. For example, an individual velocity may be calculated for each individual and may be combined to determine the group flow velocity. In these examples, a benchmark group flow velocity corresponds to a threshold exposure level for the individuals, because the group flow velocity is predictive of how long the individuals will remain in the UV light zone 300, and the amount of time spent in the UV light zone is predictive of the exposure level for each individual.

A controller may receive data (e.g., image data) from the motion sensor device, and use this data to determine how quickly each individual is moving through the UV light zone 300. In FIG. 3A, a first group flow velocity 310 is below the benchmark group flow velocity. In response to determining that the first group flow velocity 310 is below the benchmark group flow velocity, the controller causes the UV light source to reduce a level of UV light emitted towards the UV light zone 300 from a first light level to a second light level. This ensures that, after exiting the UV light zone 300, the individuals will have been exposed to a UV light level that is less than the threshold exposure level.

Figure 3B:
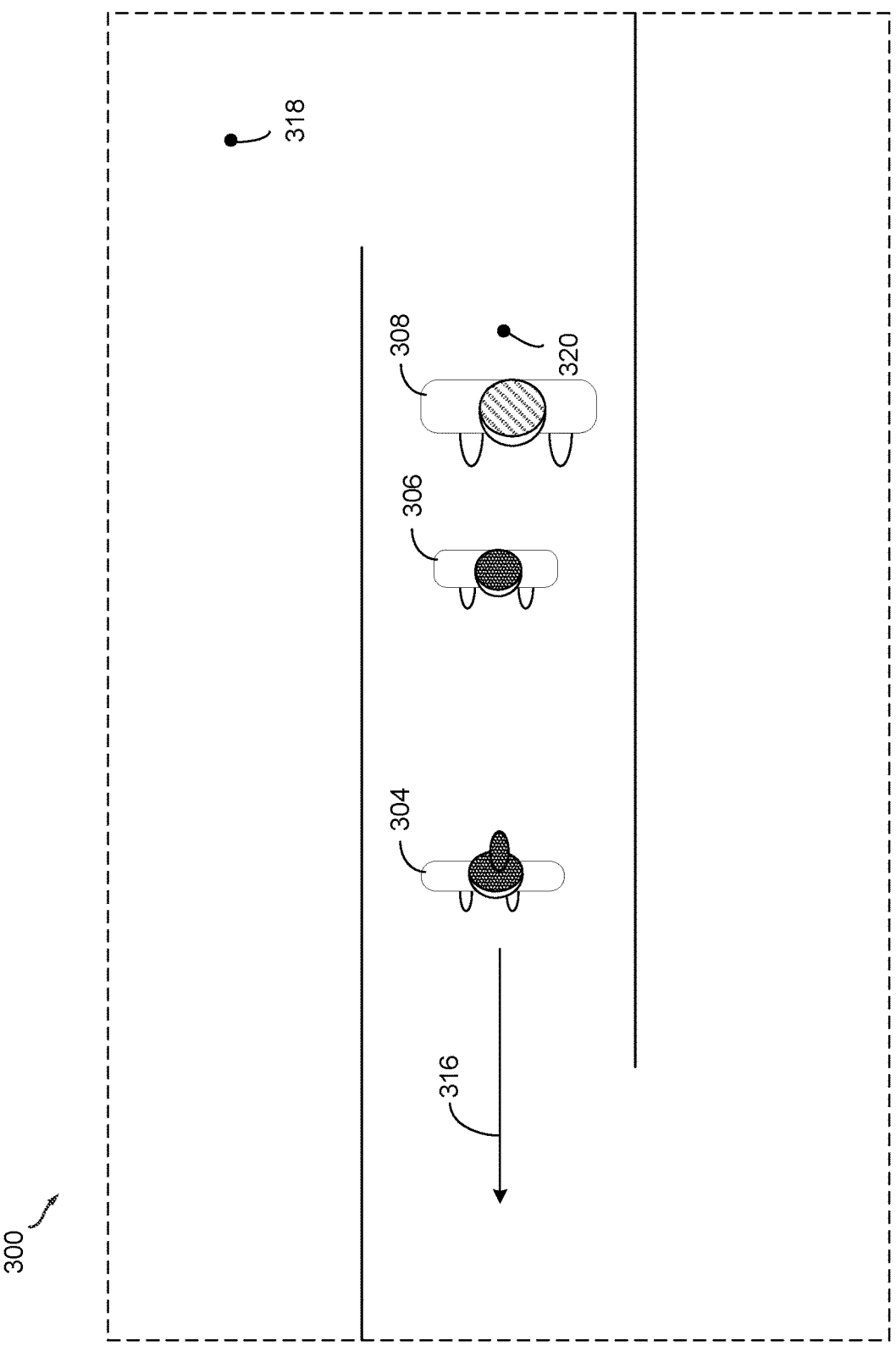
FIG. 3B illustrates a UV light zone at a second time, according to an example implementation.

FIG. 3B illustrates the UV light zone 300 at a second time, according to an example implementation. In particular, FIG. 3B shows that the first individual 304, the second individual 306, and the third individual 308 have moved through the queue, and that the first group flow velocity 310 has been updated to a second group flow velocity 316. The second group flow velocity 316 is determined based on an average period of time for the one or more individuals to move from a third point 318 of the UV light zone 300 to a fourth point 320 of the UV light zone. The second group flow velocity is above the benchmark group flow velocity. In response to determining that the second group flow velocity 316 is above the benchmark group flow velocity the controller of the sanitization system causes the UV light source to increase a level of UV light emitted towards the UV light zone 300 from the second light level to the first light level. In this manner, the sanitization system can proactively adjust the light level of the UV light source to ensure that individuals in the UV light zone are exposed to an appropriate level of UV light while also disinfecting the UV light zone 300.

Figure 4:
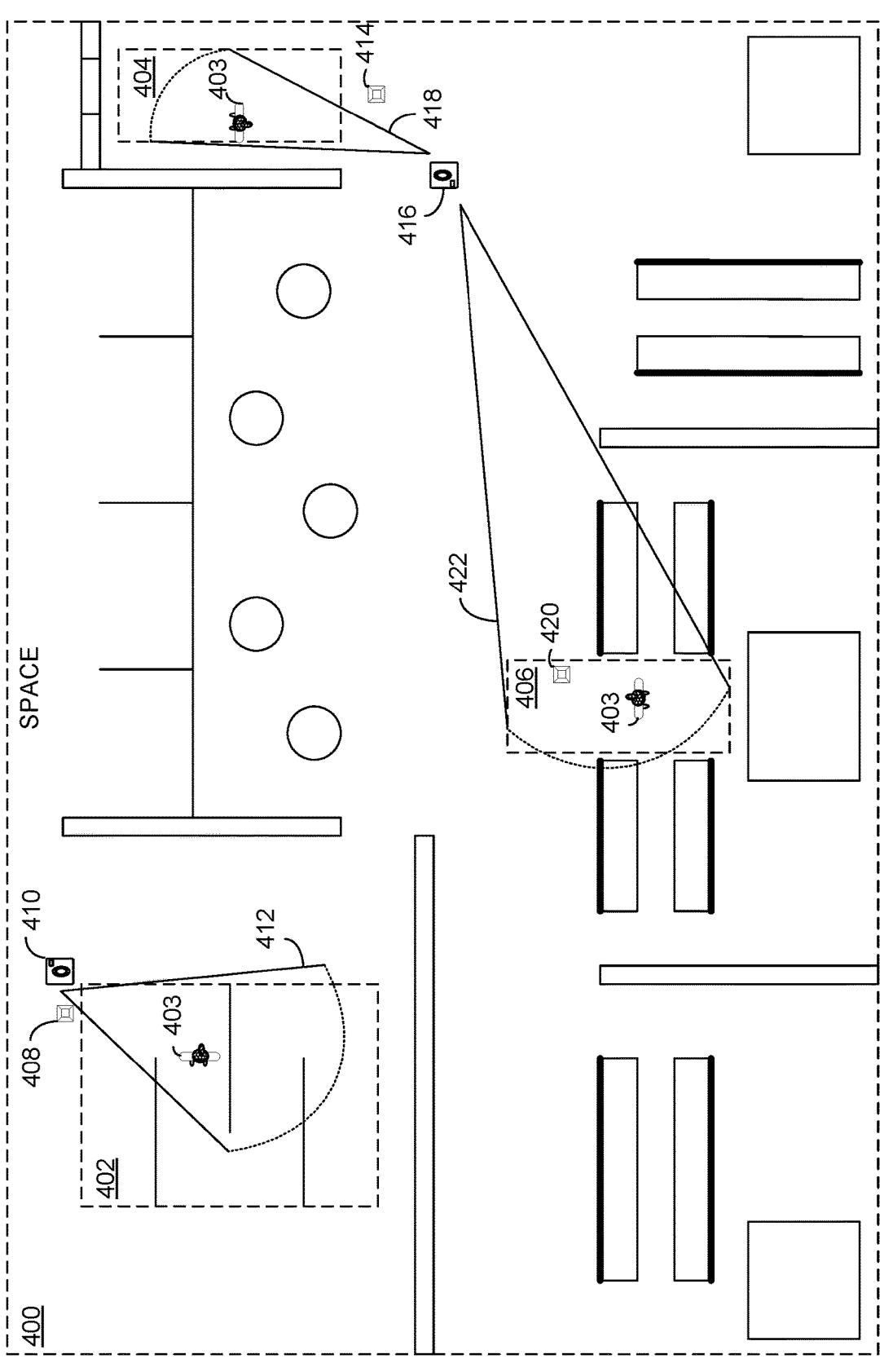
FIG. 4 illustrates a sanitization system operating in an environment having a plurality of UV light zones, according to an example implementation.

FIG. 4 illustrates a sanitization system operating in an environment having a plurality of UV light zones, according to an example implementation. In particular, FIG. 4 shows a space 400 that includes a first UV light zone 402, a second UV light zone 404, and a third UV light zone 406. Each of the UV light zones may correspond to areas with relatively high congestion of individuals in the space 400. For example, each UV light zone may correspond to a queue, hallway, doorway, or another area of the space 400 where human traffic is expected.

FIG. 4 shows an illustrative example of an interior of a building that includes a security line queue, a lavatory hallway, and an exit path. For example, the building can be an airport, train station, museum, library, or another building where several individuals may congregate. The first UV light zone 402 corresponds to the security line queue the second UV light zone 404 corresponds to the lavatory hallway, and the third UV light zone 406 corresponds to the exit path.

A sanitization system is configured to monitor movements of individuals in the space 400, and to emit UV light based at least in part on the movements of the individuals. A server may store data that represents movements of each individual in the space 400, characteristics of different UV lights zones, and exposure parameter values for each individual. A controller of the sanitization system can use this information to control UV light sources in the environment. For illustrative purposes, an individual 403 is shown in different positions in the space 400, and the following description of FIG. 4 relates to movements of the individual 403 within the space 400.

The sanitization system includes a First UV light source 408 and a motion sensor device 410, which correspond to the first UV light zone 402. As the individual 403 moves through the security line queue within the first UV light zone, the motion sensor device 410 senses movements of the individual 403. For example, the motion sensor device 410 may include an image capture device with a first field of view 412 that covers the first UV light zone 402, and may use facial recognition techniques to track movements of the individual 403. In other examples, the motion sensor device may generate data (e.g., image data) used to track movements of the individual 403. The motion sensor device 410 may alternatively include an IR tracking sensor, a LIDAR device, or another device capable of tracking positions of individuals in the first UV light zone 402. In the example shown in FIG. 4, the controller of the sanitization system tracks an exposure parameter value (e.g., a total exposure level) of the individual 403 as the individual 403 moves through the first UV light zone 402. In the example scenario of FIG. 4, the UV light level of the First UV light source 408 remains constant within the first UV light zone 402 because the exposure parameter value of the individual 403 has not exceeded a threshold value and no other individuals in the security queue have an exposure parameter value that exceeds the threshold value.

After exiting the first UV light zone 402, the individual 403 enters the second UV light zone 404 corresponding to the lavatory hallway. The sanitization system includes a second UV light source 414 and a second motion sensor device 416, which correspond to the second UV light zone 404. As the individual 403 moves through the lavatory hallway within the second UV light zone 404, the second motion sensor device 416 senses movements of the individual 403. For example, the second motion sensor device 416 may include an image capture device with a second field of view 418 that covers the second UV light zone 404, and may generate data for use in tracking movements of the individual 403. In the example scenario of FIG. 4, the controller reduces the UV light level of the second UV light source 414 because, though the exposure parameter value of the individual 403 has not exceeded the threshold value, an exposure parameter value of one or more other individuals in the second UV light zone 404 has exceeded the threshold value.

After exiting the first UV light zone 402 and the second UV light zone 404, the individual 403 enters the third UV light zone 406 corresponding to the exit path. The sanitization system further includes a third UV light source 420, which corresponds to the second UV light zone 404. As the individual 403 moves through the exit path within the third UV light zone 406, the second motion sensor device 416 senses movements of the individual 403. For example, the second motion sensor device 416 may have a third field of view 422 that covers the third UV light zone 406, and may generate data for use in tracking movements of the individual 403. In the example scenario of FIG. 4, the controller reduces the UV light level of the second UV light source 414 because the exposure parameter value of the individual 403 has exceeded the threshold value. For example, the controller may cause the third UV light source 420 to avoid emitting light towards the individual 403, or may stop emitting light toward the third UV light zone 406 altogether.

The example scenario described with respect to the individual 403 involves using a controller of a sanitization system to track movements of the individual 403 in a plurality of different UV light zones with different UV light levels, and to adjust UV light levels in each UV light zone differently based on an exposure parameter level of the individual 403 and other individuals in the space 400. Further, as shown in FIG. 4, a single feature of a sanitization system (e.g., the controller or the second motion sensor device 416) can be associated with multiple different UV light zones. Still further, though a single controller is described with respect to FIG. 4, a plurality of controllers can be used within the sanitization system. For example, each UV light source or motion sensor device may correspond to a different controller, and each controller may interact with one another or with a server in order to control UV light levels within the space 400.

Though FIG. 4 shows a particular arrangement of an interior of a building, other arrangements are possible, and similar sanitization systems may be implemented in other places, such as in a commercial aircraft, in a train, in a bus, or in an outdoor venue.

FIG. 5 illustrates a flowchart of a method 500 for sanitizing a space (e.g., the space 400), according to an example implementation. The method 500 shown in FIG. 5 presents an example of a method that could be used with the sanitization system 100 or with components of thereof. Further, the functions described with respect to FIG. 5 may be supplemented by, replaced by, or combined with functions described above with respect to FIGS. 2-4. Further, devices or systems may be used or configured to perform logical functions presented in FIG. 5.

In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 500 may include one or more operations, functions, or actions as illustrated by one or more of blocks 502-510. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 5, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 502, the method 500 includes controlling, by the controller 102 of the sanitization system 100, the UV light source 112 to emit UV light towards the UV light zone 111 at a UV light level. For example, the controller may cause the UV light source 112 at a given intensity, brightness, or power level.

At block 504, the method 500 includes receiving, by the controller 102 from the motion sensor device 114, data that indicates movements of one or more individuals within the UV light zone 111. For example, the data may include image data used for facial recognition techniques to identify positions of particular individuals in the UV light zone 111 at different times, IR tracking sensor data used for feature tracking to identify positions of particular individuals in the UV light zone 111 at different times, or LIDAR data used for feature tracking to identify positions of particular individuals in the UV light zone 111 at different times.

At block 506, the method 500 includes determining, by the controller 102 based on the movements of one or more individuals within the UV light zone 111, an exposure parameter value for each of the one or more individuals in the UV light zone 111. For example, the controller 102 may use the movements of the one or more individuals to determine an amount of time that each user is exposed to UV light, or to track a total exposure level for each user.

At block 508, the method 500 includes determining, by the controller 102, that the exposure parameter value of at least one of the one or more individuals exceeds a threshold value. For example, the threshold value may be a threshold amount of time of UV exposure or a threshold amount of UV exposure. The threshold value may be the first of a plurality of threshold values, and each threshold value may result in a different action by the controller 102.

At block 510, the method 500 includes, responsive to determining that the exposure parameter value of at least one of the one or more individuals exceeds the threshold value, causing, by the controller 102, the UV light source 112 to reduce the UV light level of the UV light emitted towards the UV light zone 111. In this manner, the sanitization system 100 can effectively disinfect an area within threshold constraints associated with the exposure parameter value for each individual in the UV light zone 111.

Within examples, the exposure parameter value includes an elapsed time that the one or more individuals are exposed to the UV light within the UV light zone 111, and the threshold value includes a threshold elapsed time. In these examples, causing the UV light source 112 to reduce the UV light level of the UV light includes causing the UV light source 112 to reduce the UV light level based on determining that a respective elapsed time for a respective individual occupant exceeds the threshold elapsed time. In related examples, the motion sensor device includes an image capture device. The one or more individuals include a plurality of individuals. In these examples, method 500 further includes identifying, by the controller 102, different individuals of the plurality of individuals based on images captured by the image capture device, and determining that a first exposure parameter value of a first individual occupant has exceeded the threshold elapsed time. In these examples, causing the UV light source 112 to reduce the UV light level of the UV light includes causing the UV light source 112 to reduce the UV light level in an area associated with the first individual occupant within the UV light zone 110 and maintaining the UV light level in a another area of the UV light zone. For example, this may be performed as described above with respect to FIG. 2.

Within examples, the exposure parameter value includes a total exposure level. In these examples, the method 500 further includes monitoring, by the controller 102, the total exposure level for each of the one or more individuals based on the UV light level of the UV light and an elapsed time that each of the one or more individuals are exposed to UV light within the UV light zone 111. In these examples, causing the UV light source 112 to reduce the UV light level of the UV light emitted towards the UV light zone 111 includes causing the UV light source 112 to reduce the UV light level based on determining that the total exposure level for at least one of the one or more individuals has exceeded a threshold total exposure level.

Within examples, the exposure parameter value includes a total exposure level and the threshold value includes a threshold exposure level. In these examples, the method 500 further includes determining a group flow velocity of the one or more individuals based on the movements of the one or more individuals sensed by the motion sensor device 114. A benchmark group flow velocity corresponds to the threshold exposure level. In these examples, determining that the exposure parameter value exceeds the threshold value includes determining that the group flow velocity is lower than the benchmark group flow velocity. In related examples, determining the group flow velocity includes determining an average period of time for the one or more individuals to move from a first point 312 of the UV light zone 111 to a second point 314 of the UV light zone 111. For example, determining the group flow velocity may be performed as described above with respect to FIG. 3A and FIG. 3B.

Within examples, the exposure parameter value includes a total exposure level and the threshold value includes a threshold exposure level. In these examples, the method 500 includes determining an expected group flow velocity of the one or more individuals based on an operational parameter associated with the UV light zone 111. For example, the operational parameter may include an expected wait time for a queue or an expected start time for an event (e.g., a movie, flight departure, lunch hour, etc.). Within examples, the group flow velocity is inversely proportional to the total exposure level. For example, a relatively high group flow velocity corresponds to a relatively low total exposure level and vice versa. In some examples, the group flow velocity may be linearly proportional to the toal exposure level. In these examples, the benchmark group flow velocity corresponds to the threshold exposure level, and determining that the exposure parameter value exceeds the threshold value includes determining that the expected group flow velocity is lower than the benchmark group flow velocity.

Within examples, the UV light zone 111 is a first UV light zone of a plurality of UV light zones within the space 400, and causing the UV light source 112 to reduce the UV light level includes causing the UV light source 112 to reduce a first UV light level in the first UV light zone and maintaining a second UV light level in a second UV light zone. In related examples, different UV light zones are associated with different UV light levels based on one or more of (i) an expected group flow velocity in each respective UV light zone and (ii) an expected order in which the one or more individuals will enter each respective UV light zone. For example, the first UV light zone 402 may have a higher light level than the second UV light zone 404 or the third UV light zone 406 based on individuals being expected to enter the first UV light zone 402 before entering the second UV light zone 404 or the third UV light zone 406.

Within examples, the UV light zone 111 is a first UV light zone of a plurality of UV light zones 110 within the space 400, the exposure parameter value includes a total exposure level, and the threshold value includes a threshold exposure level. In these examples, the method 500 further includes tracking movement of the one or more individuals within the plurality of UV light zones 110 based on data from the motion sensor device 114, and determining the total exposure level of the one or more individuals based on tracking the movements of the one or more individuals within the plurality of UV light zones 110. In these examples, causing the UV light source 112 to reduce the UV light level includes causing UV light source 112 to reduce a respective UV light level within at least one of the plurality of UV light zones 110 based on determining that a respective total exposure level exceeds the threshold exposure level.

Within examples, the UV light zone 111 is a first UV light zone of a plurality of UV light zones 110 within the space 400, and each respective UV light zone is associated with a respective UV light level. In these examples, each respective UV light level corresponds to a respective benchmark group flow velocity of individuals within a respective UV light zone. For example, the first UV light zone 402, the second UV light zone 404, and the third UV light zone 406 may have different benchmark group flow velocities based on being positioned in different areas of the space 400.

Within examples, the sanitization system 100 further includes a server 124. The exposure parameter value includes a total exposure level, and the threshold value includes a threshold exposure level. In these examples, the method 500 further includes tracking the total exposure level for each of the one or more individuals based on the UV light level of the UV light and an elapsed time that each of the one or more individuals are exposed to UV light within the UV light zone 111, and storing a representation of the total exposure level tracked for each of the one or more individuals. In these examples, one or more separate sanitization systems in a network of sanitization systems are configured to access the server 124 in order to maintain the total exposure level for each of the one or more individuals below the threshold exposure level.

Thus, the systems and methods described herein provide a framework for sanitizing a space while maintaining exposure parameter levels of individuals below a threshold level. By tracking movements of each individual in one or more UV light zones, a sanitization system can optimize a process for disinfecting a space in order to reduce the risk of transferring diseases between individuals.

By the term "substantially," "similarity," and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

By the term "simultaneously," it is meant that at least a portion of two different functions are being performed contemporaneously. For example, by referring to a plurality of objects being manufactured simultaneously, it is meant that two or more objects are contemporaneously disposed on a conveyor system used for manufacturing the objects.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A sanitization system for a space, comprising:

an ultraviolet (UV) light source configured to emit UV light towards a UV light zone at a UV light level;

a motion sensor device configured to sense movements of one or more individuals in the UV light zone; and a controller in communication with the motion sensor device and the UV light source, wherein the controller is configured to:

determine, based on the movements of the one or more individuals sensed by the motion sensor device, an exposure parameter value for each of the one or more individuals in the UV light zone, wherein the exposure parameter value comprises a total exposure level, determine that the exposure parameter value determined for at least one of the one or more individuals exceeds a threshold value, wherein the threshold value comprises a threshold exposure level, and responsive to determining that the exposure parameter value determined for the at least one individual exceeds the threshold value, cause the UV light source to reduce the UV light level of the UV light emitted towards a part of the UV light zone that includes the at least one individual to a first reduced UV light level while maintaining the UV light level of the UV light emitted towards another part of the UV light zone, wherein the first reduced UV light level corresponds to the exposure parameter value to prevent the at least one individual from experiencing an unsafe UV light exposure, determine a group flow velocity of the one or more individuals based on the movements of the one or more individuals sensed by the motion sensor device, wherein determining the group flow velocity of the one or more individuals comprises for a group of more than two of the one or more individuals, measuring an individual flow velocity for each individual in the group from a first point to a second point in the UV light zone and calculating an average individual flow velocity of the group, wherein the group flow velocity is equal to the calculated average individual flow velocity of the group, wherein a benchmark group flow velocity corresponds to the threshold exposure level, and responsive to determining that the group flow velocity is lower than the benchmark group flow velocity, cause the UV light source to reduce the UV light level of the UV light emitted towards the UV light zone to a second reduced UV light level, wherein the second reduced UV light level corresponds to the threshold exposure level to prevent the group from experiencing an unsafe UV light exposure.

2. The sanitization system of claim 1, wherein the motion sensor device comprises an image capture device, wherein the one or more individuals comprise a plurality of individuals, and wherein the controller is further configured to:

identify different individuals of the plurality of individuals based on images captured by the image capture device; and determine that a first exposure parameter value of a first individual occupant has exceeded the threshold elapsed time, wherein causing the UV light source to reduce the UV light level of the UV light comprises causing the UV light source to reduce the UV light level in an area associated with the first individual occupant within the UV light zone and maintaining the UV light level in another area of the UV light zone.

3. The sanitization system of claim 1, wherein the controller is further configured to:

monitor the total exposure level for each of the one or more individuals based on the UV light level of the UV light and an elapsed time that each of the one or more individuals are exposed to UV light within the UV light zone, and wherein causing the UV light source to reduce the UV light level of the UV light emitted towards the UV light zone comprises causing the UV light source to reduce the UV light level based on determining that the total exposure level for at least one of the one or more individuals has exceeded a threshold total exposure level.

4. The sanitization system of claim 1, wherein the exposure parameter value comprises an elapsed time that the one or more individuals are exposed to the UV light within the UV light zone, wherein the threshold value comprises a threshold elapsed time.

5. The sanitization system of claim 1, wherein determining the group flow velocity comprises determining an average period of time for the one or more individuals to move from a first point of the UV light zone to a second point of the UV light zone.

6. The sanitization system of claim 1, wherein the controller is further configured to:

determine an expected group flow velocity of the one or more individuals based on an operational parameter associated with the UV light zone, wherein determining that the exposure parameter value exceeds the threshold value comprises determining that the expected group flow velocity is lower than the benchmark group flow velocity.

7. The sanitization system of claim 1, wherein the UV light zone is a first UV light zone of a plurality of UV light zones within the space, and wherein causing the UV light source to reduce the UV light level comprises causing the UV light source to reduce a first UV light level in the first UV light zone and maintaining a second UV light level in a second UV light zone.

8. The sanitization system of claim 7, wherein different UV light zones are associated with different UV light levels based on one or more of (i) an expected group flow velocity in each respective UV light zone and (ii) an expected order in which the one or more individuals will enter each respective UV light zone.

9. The sanitization system of claim 1, wherein the UV light zone is a first UV light zone of a plurality of UV light zones within the space, wherein the controller is further configured to:
   track the movements of the one or more individuals within the plurality of UV light zones based on data from the motion sensor device, and
   determine the total exposure level of the one or more individuals based on tracking the movements of the one or more individuals within the plurality of UV light zones,
   wherein causing the UV light source to reduce the UV light level comprises causing UV light to reduce a respective UV light level within at least one of the plurality of UV light zones based on determining that a respective total exposure level exceeds the threshold exposure level.

10. The sanitization system of claim 1, wherein the UV light zone is a first UV light zone of a plurality of UV light zones within the space, and wherein each respective UV light zone is associated with a respective UV light level.

11. The sanitization system of claim 10, wherein each respective UV light level corresponds to a respective benchmark group flow velocity of individuals within a respective UV light zone.

12. The sanitization system of claim 1, further comprising a server, wherein the controller is further configured to:
   track the total exposure level for each of the one or more individuals based on the UV light level of the UV light and an elapsed time that each of the one or more individuals are exposed to UV light within the UV light zone; and
   store a representation of the total exposure level tracked for each of the one or more individuals,
   wherein one or more separate sanitization systems in a network of sanitization systems are configured to access the server in order to maintain the total exposure level for each of the one or more individuals below the threshold exposure level.

13. The sanitization system of claim 1, further comprising a movable component that is configured to cause the UV light source to adjust a direction, a beam angle, or a beam spread of UV light emitted by the UV light source and wherein causing the UV light source to reduce the UV light level of the UV light comprises causing the UV light source to avoid emitting UV light toward a respective individual whose exposure parameter value has reached the threshold value.

14. A method for sanitizing a space, comprising:
   controlling, by a controller of a sanitization system, an ultraviolet (UV) light source to emit UV light towards a UV light zone at a UV light level;

receiving, by the controller from a motion sensor device, data that indicates movements of one or more individuals within the UV light zone;
   determining, by the controller based on the movements of the one or more individuals within the UV light zone, an exposure parameter value for each of the one or more individuals in the UV light zone;
   determining, by the controller, that the exposure parameter value of at least one individual of the one or more individuals exceeds a threshold value, wherein the threshold value comprises a threshold exposure level, and responsive to determining that the exposure parameter value determined for the at least one individual exceeds the threshold value, cause the UV light source to reduce the UV light level of the UV light emitted towards a part of the UV light zone that includes the at least one individual to a first reduced UV light level while maintaining the UV light level of the UV light emitted towards another part of the UV light zone, wherein the first reduced UV light level corresponds to the exposure parameter value to prevent the at least one individual from experiencing an unsafe UV light exposure,
   determining, by the controller, a group flow velocity of the one or more individuals based on the movements of the one or more individuals sensed by the motion sensor device, wherein determining the group flow velocity of the one or more individuals comprises for a group of more than two of the one or more individuals, measuring an individual flow velocity for each individual in the group from a first point to a second point in the UV light zone and calculating an average individual flow velocity of the group, wherein the group flow velocity is equal to the calculated average individual flow velocity of the group, wherein a benchmark group flow velocity corresponds to the threshold exposure level, and
   responsive to determining that the group flow velocity is lower than the benchmark group flow velocity, cause the UV light source to reduce the UV light level of the UV light emitted towards the UV light zone to a second reduced UV light level, wherein the second reduced UV light level corresponds to the threshold exposure level to prevent the group from experiencing an unsafe UV light exposure.

15. The method of claim 14, wherein the exposure parameter value comprises a total exposure level, the method further comprising:
   tracking, by the controller, the total exposure level for each of the one or more individuals based on the UV light level of the UV light and an elapsed time that each of the one or more individuals are exposed to UV light within the UV light zone,
   wherein causing the UV light source to reduce the UV light level of the UV light emitted towards the UV light zone comprises causing the UV light source to reduce the UV light level based on determining that the total exposure level for at least one of the one or more individuals has exceeded a threshold total exposure level.

16. The method of claim 14, wherein the exposure parameter value comprises a total exposure level
   wherein the group flow velocity is inversely proportional to the total exposure level, and wherein determining that the exposure parameter value exceeds the threshold value comprises determining that the group flow velocity is lower than the benchmark group flow velocity.

17. The method of claim 14, wherein the exposure parameter value comprises a total exposure level, the method further comprising:

determining, by the controller, an expected group flow velocity of the one or more individuals based on an operational parameter associated with the UV light zone, wherein the expected group flow velocity is inversely proportional to the total exposure level, and wherein a benchmark group flow velocity corresponds to the threshold exposure level, wherein determining that the exposure parameter value exceeds the threshold value comprises determining that the expected group flow velocity is lower than the benchmark group flow velocity.

18. The method of claim 14, wherein the exposure parameter value comprises an elapsed time that the one or more individuals are exposed to the UV light within the UV light zone, wherein the threshold value comprises a threshold elapsed time, and wherein causing the UV light source to reduce the UV light level comprises causing the UV light source to reduce the UV light level based on determining that a respective elapsed time for a respective individual occupant exceeds the threshold elapsed time.

19. The method of claim 14, wherein the exposure parameter value comprises a total exposure level, the method further comprising:

tracking, by the controller, the total exposure level for each of the one or more individuals based on the UV light level of the UV light and an elapsed time that each of the one or more individuals are exposed to UV light within the UV light zone; and storing, by the controller, a representation of the total exposure level tracked for each of the one or more individuals in a server, wherein one or more separate sanitization systems in a network of sanitization systems are configured to access the server in order to maintain the total exposure level for each of the one or more individuals below the threshold exposure level.

20. A non-transitory computer readable medium having instructions stored thereon that, when executed by one or more processors cause a controller of a sanitization system to perform functions comprising:

controlling an ultraviolet (UV) light source to emit UV light towards a UV light zone at a UV light level;

receiving, from a motion sensor device, data that indicates movements of one or more individuals within the UV light zone;

determining, based on the movements of the one or more individuals within the UV light zone, an exposure parameter value for each of the one or more individuals in the UV light zone;

determining that the exposure parameter value of at least one individual of the one or more individuals exceeds a threshold value, wherein the threshold value comprises a threshold exposure level, and responsive to determining that the exposure parameter value determined for the at least one individual exceeds the threshold value, cause the UV light source to reduce the UV light level of the UV light emitted towards a part of the UV light zone that includes the at least one individual to a first reduced UV light level while maintaining the UV light level of the UV light emitted towards another part of the UV light zone, wherein the first reduced UV light level corresponds to the exposure parameter value to prevent the at least one individual from experiencing an unsafe UV light exposure, determining, by the controller, a group flow velocity of the one or more individuals based on the movements of the one or more individuals sensed by the motion sensor device, wherein determining the group flow velocity of the one or more individuals comprises for a group of more than two of the one or more individuals, measuring an individual flow velocity for each individual in the group from a first point to a second point in the UV light zone and calculating an average individual flow velocity of the group, wherein the group flow velocity is equal to the calculated average individual flow velocity of the group, wherein a benchmark group flow velocity corresponds to the threshold exposure level, and responsive to determining that the group flow velocity is lower than the benchmark group flow velocity, cause the UV light source to reduce the UV light level of the UV light emitted towards the UV light zone to a second reduced UV light level, wherein the second reduced UV light level corresponds to the threshold exposure level to prevent the group from experiencing an unsafe UV light exposure.

* * * * *